United States Patent [19]

Vignau et al.

[11] 4,205,072

[45] May 27, 1980

[54] 3-CARBAMOYLOXYMETHYL-7-(AMINO-4-THIAZOLYL-ACETAMIDO)-CEPHALOSPORANIC ACID DERIVATIVES

[75] Inventors: Michel Vignau, Neuilly-sur-Seine; André Lutz, Strasbourg, both of France

[73] Assignee: Roussel Uclaf, Paris, France

[21] Appl. No.: 765,439

[22] Filed: Feb. 4, 1977

[30] Foreign Application Priority Data

Feb. 5, 1976 [FR] France ............................... 76 03210

[51] Int. Cl.$^2$ ............................................ C07D 501/20
[52] U.S. Cl. ..................................... 424/246; 544/16
[58] Field of Search ..................... 260/243 C; 424/246; 544/16

[56] References Cited

U.S. PATENT DOCUMENTS

| 3,907,787 | 9/1975 | Teller et al. ........................ 260/243 C |
| 3,926,984 | 12/1975 | Teller et al. ....................... 260/243 C |

FOREIGN PATENT DOCUMENTS 2313069 6/1976 France .

*Primary Examiner*—Nicholas S. Rizzo
*Attorney, Agent, or Firm*—Hammond & Littell, Weissenberger and Muserlian

[57] ABSTRACT

A compound of the formula

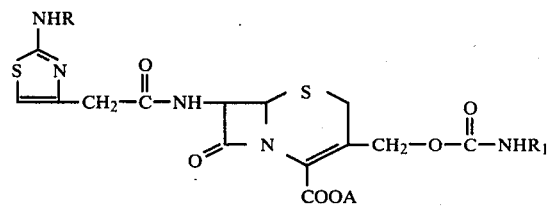

wherein R is selected from the group consisting of hydrogen and a group easily removable by acid hydrolysis or hydrogenolysis, $R_1$ is selected from the group consisting of hydrogen and alkyl of 1 to 4 carbon atoms and A is selected from the group consisting of hydrogen, alkali metal, an equivalent of alkaline earth metal and magnesium and an organic amine base having antibiotic properties and a process for their preparation and novel intermediates.

13 Claims, No Drawings

3-CARBAMOYLOXYMETHYL-7-(AMINO-4-THIAZOLYL-ACETAMIDO)-CEPHALOSPORANIC ACID DERIVATIVES

STATE OF THE ART

French Pat. No. 2,255,077 and French BSM No. 2899 M disclose cephalosporins substituted in the 3-position with different substituents.

OBJECTS OF THE INVENTION

It is an object of the invention to provide the novel 3-carbamoyloxymethyl-cephalosporins of formula I and to provide a novel process and novel intermediates therefore.

It is a further object of the invention to provide novel antibiotic compositions and a novel method of combatting bacterial infections in warm-blooded animals.

These and other objects and advantages of the invention will become obvious from the following detailed description.

THE INVENTION

The novel compounds of the invention have the formula

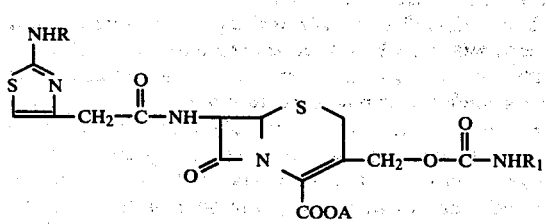

wherein R is selected from the group consisting of hydrogen and a group easily removable by acid hydrolysis or hydrogenolysis, $R_1$ is selected from the group consisting of hydrogen and alkyl of 1 to 4 carbon atoms and A is selected from the group consisting of hydrogen, alkali metal, an equivalent of alkaline earth metal and magnesium and an organic amine base.

The groups easily removable by acid hydrolysis or by hydrogenolysis are well known in cephalosporin chemistry and examples thereof are tert.-butoxycarbonyl, trityl, benzyl, dibenzyl, trichloroethyl, carbobenzyloxy, formyl, trichloroethoxycarbonyl or 2-tetrahydropyranyl. $R_1$ may also be alkyl, such as methyl, ethyl, propyl, isopropyl, butyl, sec.-butyl and tert.-butyl.

Examples of A are hydrogen, potassium, sodium, lithium, calcium, magnesium, trimethylamine, triethylamine, methylamine, propylamine, N,N-dimethylethanolamine, tris-(hydroxymethyl)-methylamine, arginine or lysine.

The groups easily removable by acid hydrolysis or hydrogenolysis that are preferred are tert.-butoxycarbonyl, trityl, dibenzyl, trichloroethyl and carbobenzyloxy.

Among the preferred compounds of formula I, R is hydrogen or trityl, $R_1$ is hydrogen or methyl and A is hydrogen. Particularly preferred is 3-carbamoyloxymethyl-7β-[2-(2-amino-4-thiazolyl)-acetamido]-ceph-3-eme-4-carboxylic acid.

The novel products of the invention exist either in the form of formula I or in the form of the formula

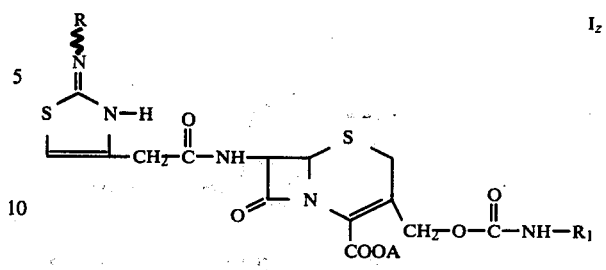

wherein A, R and $R_1$ have the above definition.

The novel process of the invention for the preparation of compounds of formula I comprises either reacting 7-amino-cephalosporanic acid with an alkali metal alcoholate in a lower alkanol and then with an acid of the formula

or a functional derivative thereof wherein R' is a group easily removable by acid hydrolysis or hydrogenolysis to form a compound of the formula

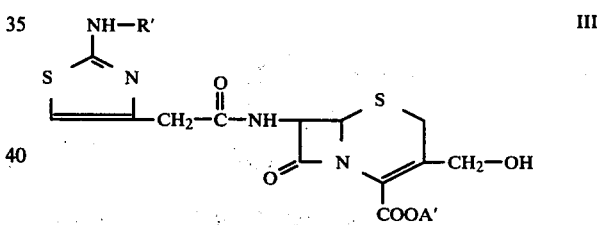

wherein A' is an alkali metal or reacting a product of the formula

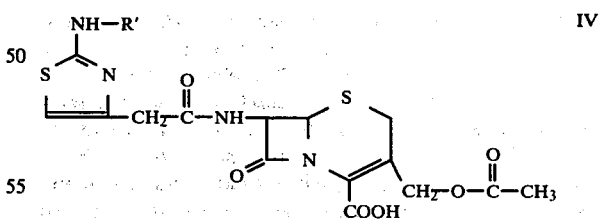

with an alkali metal alcoholate in a lower alkanol to obtain a compound of formula III. The compound of formula III is then either reacted with an isocyanate of the formula

wherein $R_2$ is a group easily removable by hydrolysis to obtain a compound of the formula

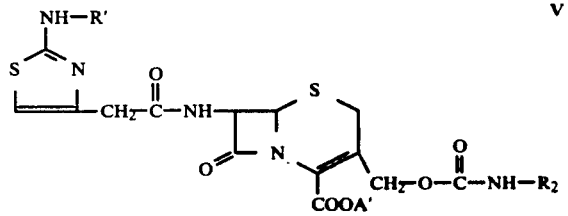

which then is treated with an hydrolysis agent and then eventually with an acid when using a basic hydrolysis agent to obtain a compound of the formula

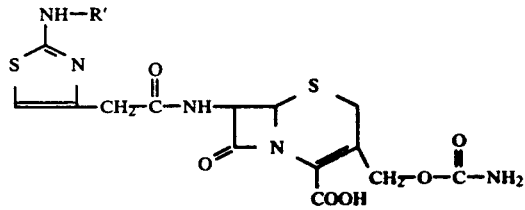

or reacted with an isocyanate of the formula

wherein $R_1'$ is alkyl of 1 to 4 carbon atoms to obtain a compound of the formula

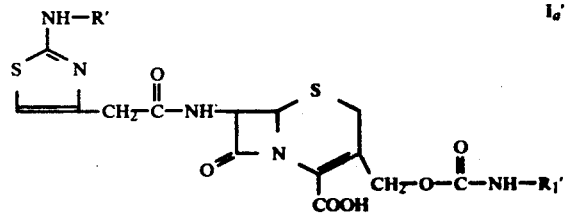

and the compounds of formula Ia or Ia' may be subjected to acid hydrolysis or hydrogenolysis to obtain a compound of formula I wherein R, $R_1$ and A are hydrogen and R and A are hydrogen and $R_1$ is alkyl of 1 to 4 carbon atoms, respectively and the free acids may be salified by known methods.

In a preferred mode of the process of the invention, 7-amino-cephalosporanic acid is treated with sodium methoxide in methanol but other alcoholates such as potassium tert.-butylate in alkanols of 1 to 3 carbon atoms may be used. The acid of formula II is preferably used in the form of its acid chloride or its anhydride formed in situ by reaction with isobutyl chloroformate. However, also useful are other acid halides and acid anhydrides formed in situ with other alkyl chloroformates, dialkylcarbodiimides or dicycloalkylcarbodiimides such as dicyclohexylcarbodiimide. Equally useful are other functional acid derivatives such as acid azide, acid amide or acid ester formed, for example, with hydroxy succinimide, p-nitrophenol or 2,4-dinitrophenol. If the acid halide is used, the reaction is preferably effected in the presence of a basic agent such as an alkali metal carbonate and bicarbonate or a tertiary organic amine such as N-methyl-morpholine, pyridine or trialkylamines such as triethylamine. The compound of formula III is also obtained by treating a compound of formula IV with an alkali metal alcoholate such as sodium methoxide in an alkanol of 1 to 3 carbon atoms.

The reaction of the compound of formula III with an isocyanate of the formula $R_2-N=C=O$ is preferably effected in one or more inert solvents such as methylene chloride but other solvents such as dimethylformamide or tetrahydrofuran may be used. The isocyanate may also be used pure. The hydrolysis of the product of formula V is preferably effected in a basic medium such as sodium bicarbonate in water but also useful are potassium bicarbonate or an alkali metal carbonate in water or a water-alcohol mixture. The resulting salt is preferably treated with dilute hydrochloric acid to form the free acid but also useful are sulfuric acid or phosphoric acid.

The product of formula V may also be hydrolyzed in acid media to directly obtain a compound of formula Ia and a slightly acid buffer media is used.

The reaction of a compound of formula III with an isocyanate of the formula $R_1'-N=C=O$ is preferably effected in dimethylformamide but equally useful are methylene chloride, tetrahydrofuran or a mixture of solvents, but the isocyanate may also be used pure. The acid hydrolysis agent is preferably trifluoroacetic acid, formic acid or acetic acid which are used in anhydrous or aqueous medium. The hydrogenolysis agent is preferably a zinc-acetic acid system.

The preferred acid hydrolysis agents to remove trityl or tert.-butoxycarbonyl groups are anhydrous trifluoroacetic acid or aqueous formic acid or acetic acid. The trichloroethyl group is preferably removed with a zinc-acetic acid system and benzyl, dibenzyl and carbobenzyloxy groups are preferably removed by catalytic hydrogenation. The salification may be effected by known methods such as by reacting the acids with a mineral base such as sodium or potassium hydroxide or sodium carbonate or bicarbonate or an organic amine base such as triethylamine. The reaction is preferably conducted in or more solvents such as water, methanol, ethanol, acetone or dioxane.

The $R_2$ group easily removable by hydrolysis is preferably trichloroacetyl, benzyl, p-methoxybenzyl or chlorosulfonyl.

The antibiotic compositions of the invention are comprised of an antibiotically effective amount of at least one compound of formula I and an inert pharmaceutical carrier. The compositions may be in the form of tablets, dragees, gelules, granules, suppositories, injectable solutions or suspensions, creams, pomades, gels, etc. prepared in the usual fashion.

Examples of suitable excipients or pharmaceutical carriers are talc, arabic gum, lactose, starch, magnesium stearate, cacao butter, aqueous or non-aqueous vehicles, fatty bodies of vegetable or animal origin, paraffinic derivatives, glycols, preservatives, diverse wetting agents, dispersants and emulsifiers.

The compositions of the invention possess very good antibiotic activity against gram positive bacteria such as staphylococcus, streptococcus, particularly penicillin resistant staphylococcus as well as against gram negative bacteria such as coliform bacteria, Klebsiella, Salmonella and Proteus.

The compositions are therefore useful in the treatment of germ sensitive infections and particularly those of staphylococcia such as staphylococcal septicemia, malignant staphylococcia on the face or skin, pyodermatitis, septic or suppurantes sores, anthrax, phlegmons, eresipels, acute primitive or post-grip staphylococcia, bronchopneumonia or pulmonary suppurations. They are equally useful for the treatment of collibacillosis and associated infections, infections of Proteus, Klebsiella and Salmonella and other infections caused by gram negative bacteria.

The novel method of the invention for combatting bacterial infections in warm-blooded animals, including humans, comprises administering to warm-blooded animals an antibacterially effective amount of at least one compound of formula I. The compounds may be administered orally, rectally, parenterally or locally by topical application to the skin or mucous. The usual daily dose is 5 to 80 mg/kg depending upon the specific compound and the method of administration.

The novel intermediates of the invention have the formula

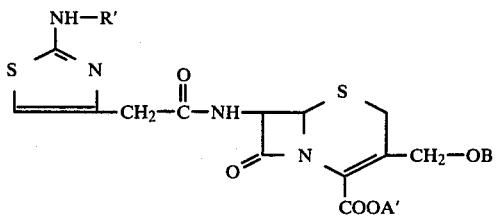

wherein R' is a group easily removable by acid hydrolysis or hydrogenolysis, A' is an alkali metal and B is selected from the group consisting of hydrogen and

and $R_2$ is a group easily removable by hydrolysis.

The acids of formula II may be made by known procedures for protection of amine functions applied to 2-amino-4-thiazolyl-acetic acid or its esters. The compounds of formula IV are prepared by reaction of 7-amino-cephalosporanic acid with an acid of formula II.

In the following examples there are described several preferred embodiments to illustrate the invention. However, it is to be understood that the invention is not intended to be limited to the specific embodiments.

EXAMPLE 1

3-carbamoyloxymethyl-7β-[2-(2-tritylamino-4-thiazolyl)-acetamido]-ceph-3-eme-4-carboxylic acid STEP A: sodium 3-hydroxymethyl-7β-[2-(2-tritylamino-4-thiazolyl)-acetamido]-ceph-3-eme-4-carboxylate 10 g of sodium methoxide were added with stirring under an inert atmosphere at −20° C. to a suspension of 20 g of 7-amino-cephalosporanic acid in 1250 ml of dry methanol. The mixture was stirred at −14° C. for 7 hours and was then saturated with carbon dioxide by addition of dry ice.

12.5 ml of N-methyl-morpholine were added at room temperature with stirring to a suspension of 44.5 g of 2-tritylamino-4-thiazolyl-acetic acid in 900 ml of tetrahydrofuran and the mixture was cooled to −25° C. 14.5 ml of isobutyl chloroformate were added to the mixture with vigorous stirring while keep the temperature at −20° C. and the mixture was filtered 30 minutes later. The filtrate was added to the above mixture saturated with carbon dioxide with stirring at −20° C. and after adding wash water, the mixture was stirred at −20° C. for 30 minutes and was held overnight at 5° C. The reaction mixture was slowly poured into about 10 liters of dry isopropyl ether and after standing for 2 hours, the mixture was filtered. The recovered product was washed with isopropyl ether and was dried to obtain 48.2 g of sodium 3-hydroxymethyl-7β-[2-(2-tritylamino-4-thiazolyl)-acetamido]-ceph-3-eme-4-carboxylate.

STEP B: 3-carbamoyloxymethyl-7β-[2-(2-tritylamino-4-thiazolyl)-acetamido]-ceph-3-eme-4-carboxylic acid.

8 g of raw product of Step A were added with stirring at room temperature to a solution of 8 g of trichloroacetyl isocyanate in 160 ml of dry methylene chloride and after stirring for 15 minutes, 1.6 liters of a solution of aqueous 6% sodium bicarbonate were added thereto. The mixture was stirred at room temperature overnight and was then extracted with ethyl acetate. The organic phase was removed and the aqueous phase was acidified with 6 N hydrochloric acid to a pH of 2 in the presence of ethyl acetate. The organic phase was washed with water, dried and concentrated under reduced pressure to 30 ml. The product was precipitated by addition of isopropyl ether and the mixture was filtered and dried to obtain 2.7 g of 3-carbamoyloxymethyl-7β-[2-(2-tritylamino-4-thiazolyl)-acetamido]-ceph-3-eme-4-carboxylic acid melting at about 200° C. with decomposition.

U.V. Spectrum (ethanol-DMSO):
Max.=265 nm;
$E_1^1=142$;
$\epsilon=9300$;
Thin layer chromatography —Rf=0.40 (50-45-4-1-ethyl acetate-ethanol-water-acetic acid).

EXAMPLE 2

3-carbamoyloxymethyl-7β-[2-(2-amino-4-thiazolyl)-acetamido]-ceph-3-eme-4-carboxylic acid A mixture of 475 mg of the product of Example 1 and 4.75 ml of acetic acid with 8% water was stirred for 2 hours at 50° C. and was then cooled. 47.5 ml of isopropyl ether was added and the mixture was triturated with stirring for 30 minutes. The mixture was redissolved in 6 ml of acetic acid with 8% water and the solution was stirred with activated carbon and was then filtered. 90 ml of isopropyl ether were added to the filtrate and the mixture was filtered to obtain 182 mg of 3-carbamoyloxymethyl-7β-[2(-2-amino-4-thiazolyl)-acetamido]-ceph-3-eme-4-carboxylic acid melting above 260° C.
U.V. Spectrum (ethanol-DMSO):
Max. at 257 nm;
$E_1{}^l=250$.
Thin layer chromatography: Rf=0.22 (6-2-2-ethyl acetate-ethanol-water).

EXAMPLE 3

3-methylcarbamoyloxymethyl-7β-[2-(2-tritylamino-4-thiazolyl)-acetamido]-ceph-3-eme-4-carboxylic acid 1 g of the raw product of Step A of Example 1 was added under nitrogen to a mixture of 5 ml of dimethylformamide and 0.5 ml of methyl isocyanate at 5° C. and 0.5 ml of methyl isocyanate was added thereto. After 30 minutes at 5° C., another 0.5 ml of methyl isocyanate was added and after stirring 2 hours at room temperature, the mixture was poured into 75 ml of an aqueous 6% NaHCO₃ solution. The mixture was extracted with ethyl acetate and the extracts were washed with sodium bicarbonate solution. The combined aqueous phases were added to ethyl acetate and the mixture was acidified with 6 N hydrochloric acid to a pH of 2. The mixture was decanted and the aqueous phase was extracted with ethyl acetate. The organic extracts were washed with water, dried and concentrated to dryness and the residue was empasted with isopropyl ether and was vacuum filtered. The product was taken up with methylene chloride and the solution was treated with activated carbon and was vacuum filtered. The filtrate was evaporated to dryness and the residue was crystallized from isopropyl ether to obtain 331 mg of 3-methylcarbamoyloxymethyl-7β-[2-(2-tritylamino-4-thiazolyl)-acetamido]-ceph-3-eme-4-carboxylic acid melting at about 210° C. Thin layer chromatography: Rf=0.42 (80-15-5-ethyl acetate-acetic acid-water).

EXAMPLE 4

3-methylcarbamoyloxymethyl-7β-[2-(2-amino-4-thiazolyl)-acetamido]-ceph-3-eme-4-carboxylic acid A mixture of 305 mg of the product of Example 3 in 4.5 ml of acetic acid containing 8% water was stirred at 50° C. for 2 hours and the mixture was poured into 45 ml of isopropyl ether. The mixture was stirred for 30 minutes and was vacuum filtered. The product was washed with isopropyl ether to obtain 180 mg of 3-methylcarbamoyloxymethyl-7β-[2-(2-amino-4-thiazolyl)-acetamido]-ceph-3-eme-4-carboxylic acid.
U.V. Spectrum (ethanol-DMSO):
 Max. at 256 nm;
 $E_1' = 212$.
Thin layer chromatography: Rf=0.33 (6-2-2-ethyl acetate-ethanol-water).

EXAMPLE 5 sodium 3-hydroxymethyl-7β-[2-(2-tritylamino-4-thiazolyl)-acetamido]-ceph-3-eme-4-carboxylate STEP A: 2-tritylamino-4-thiazolyl-acetic acid A mixture of 930 mg of ethyl 2-amino-4-thiazolylacetate, 25 ml of dry chloroform, 0.8 ml of triethylamine and 1.65 g of trityl chloride was stirred for 3 hours and then 3 ml of N hydrochloric acid and 5 ml of water were added thereto. The mixture was stirred and was decanted and another 3 ml of N hydrochloric acid and 5 ml of water were added to the organic phase. The mixture was decanted and the organic phase was dried and concentrated to dryness. The residue was added to 10 ml of dioxane and 6 ml of N sodium hydroxide and the mixture was stirred at 50° C. and then overnight at room temperature. The solvent was evaporated and the residue was diluted with water. The solution was washed with ether and was acidified with 0.5 ml of acetic acid. The mixture crystallized and was vacuum filtered to obtain 1.33 g of 2-tritylamino-4-thiazolyl-acetic acid which after purification by empasting with ether melted at 220° C.

STEP B: 3-acetoxymethyl-7β-[2-(2-tritylamino-4-thiazolyl)-acetamido]-ceph-3-eme-4-carboxylic acid A mixture of 801 mg of 2-tritylamino-4-thiazolylacetic acid, 10 ml of dry tetrahydrofuran and 2 ml of a molar solution of N-methyl-morpholine in tetrahydrofuran was stirred at −20° C. and 2 ml of a molar solution of isobutyl chloroformate in tetrahydrofuran were slowly added thereto. The mixture was stirred and a solution of 544 mg of 7-amino-cephalosporanic acid in 10 ml of water and 2.4 ml of a molar solution of N-methyl-morpholine in tetrahydrofuran was added thereto. The mixture was stirred with reheating and the solvent was evaporated. The residue was diluted with water and 2 ml of 2 N hydrochloric acid were added. The mixture was vacuum filtered and the product was dried to obtain 1.16 g of 3-acetoxymethyl-7β-[2-(2-tritylamino-4-thiazolyl)-acetamido]-ceph-3-eme-4-carboxylic acid.

STEP C: sodium 3-hydroxymethyl-7β-[2-(2-tritylamino-4-thiazolyl)-acetamido]-ceph-3-eme-4-carboxylate 70 mg of powdered sodium methylate were added at −18° C. with rapid stirring under an inert atmosphere to a mixture of 300 mg of the product of Step B in 14 ml of methanol and the mixture was stirred at −13° C. for 8 hours. Dry ice was added until the mixture was saturated with carbon dioxide and 98 ml of isopropyl ether were added. After standing, the mixture was vacuum filtered and the product was washed with isopropyl ether to obtain 304 mg of product containing inorganic material. The product was dissolved in tetrahydrofuran and the solution was filtered. Thin layer chromatography with elution with a 80-15-5 ethyl acetate-acetic acid-water mixture yielded sodium 3-hydroxymethyl-7β-[2-(2-tritylamino-4-thiazolyl)-acetamido]-ceph-3-eme-4-carboxylate with an Rf=0.24.

EXAMPLE 6

An injectable suspension was prepared from 500 mg of 3-carbamoyloxymethyl-7β-[2-(2-amino-4-thiazolyl)-acetamido]-ceph-3-eme-4-carboxylic acid and sufficient sterile water for a final total of 5 ml. Gelules were prepared containing 250 mg of the same acid with sufficient excipient to obtain a final weight of 400 mg.

PHARMACOLOGICAL DATA

A. In Vitro Activity

A series of test tubes received equal amounts of a sterile nutritive media and the tubes received increasing quantities of the test product. Each tube was seeded with a bacterial strain and the tubes were incubated at 37° C. for 24 or 48 hours. The degree of inhibition was determined by transillumination to determine the minimum inhibitory concentration in μg/ml and the results are reported in the following Tables.

| Product of Example 2 | | |
|---|---|---|
| | M.I.C. in μg/ml | |
| | 24 H | 48 H |
| Staphylococcus aureus UC 1061 Pen. sensible | 2 | 2 |
| Staphylococcus aureus UC 1128 Pen. resistant | 2 | 3 |
| Staphylococcus aureus Exp. n° 54 146 | 2 | 3 |
| Staphylococcus aureus ATCC 6538 | 1 | 1 |
| Streptococcus pyogenes A 561 | 0.1 | 0.1 |
| Streptococcus faecalis 5432 | 5 | 20 |
| Bacillus subtilis ATCC 6633 | 0.2 | 0.2 |
| Escherichia coli ST UC 1020 | 2 | 2 |
| Escherichia coli RT UC 1261 | 2 | 3 |
| Escherichia coli Exp. T026B6 | 5 | 5 |
| Escherichia coli RG R 55 123 D | 20 | 20 |
| Salmonella typhimurium 420 | 2 | 2 |
| Klebsiella pneumoniae Exp. 52 145 | 1 | 1 |
| Klebsiella pneumoniae 2536 R | 5 | 5 |

| Product of Example 4 | M.I.C. in µg/ml | |
|---|---|---|
| | 24 H | 48 H |
| Staphylococcus aureus UC 1061 Pen. sensible | 3 | 5 |
| Staphylococcus aureus UC 1128 Pen. resistant | 10 | 10 |
| Staphylococcus aureus Exp. n° 54 146 | 5 | 10 |
| Staphylococcus aureus ATCC 6538 | 2 | 3 |
| Streptococcus pyogenes A 561 | 0.2 | 0.2 |
| Bacillus subtilis ATCC 6633 | 0.5 | 0.5 |
| Escherichia coli ST UC 1020 | 3 | 3 |
| Escherichia coli RT UC 1261 | 2 | 3 |
| Escherichia coli Exp. T026B6 | 10 | 10 |
| Escherichia coli RG R 55 123 D | 20 | 20 |
| Klebsiella pneumoniae Exp. 52 145 | 2 | 2 |
| Proteus mirabilis (Indol -) A 235 | 5 | 5 |
| Salmonella typhimurium 420 | 5 | 5 |

B. In Vivo Activity With Experimental Staphylococcia

Groups of 10 male mice weighing about 22.5 g received intraperitoneally 0.5 ml of a 24 hour old culture of Staphylococcus aureus 54,146 in Pasteur nutritive bouillon diluted by 1/4.5 with distilled water and the mice received subcutaneously 1 hour, 5 hours and 24 hours later a determined quantity of the product of Example 2. The number of dead mice during 8 days is reported in the following Table.

| Dose in mg | Dead after hours | | | Mice alive on 8th day |
|---|---|---|---|---|
| | 6¾ | 21½ | 52 | |
| Controls | 1 | 9 | | 0/10 |
| 0.25 | | | 1 | 9/10 |
| 0.5 | | | | 10/10 |
| 1.0 | | | | 10/10 |
| 2.0 | | | | 10/10 |

C. In Vivo Activity With Proteus Mirabilis

Groups of 10 male mice weighing about 21.5 g received intraperitoneally 0.5 ml of a 24 hour old culture in Pasteur nutritive bouillon of Proteus Mirabilis No. A 235 diluted by ¼ with distilled water and then 1 hour and 5 and 24 hours later received subcutaneously a quantity of the product of Example 2 and the number of dead mice during 8 days is reported in the following Table.

| Dose in mg | Dead after hours | | | | Dead on 8th day |
|---|---|---|---|---|---|
| | 23¾ | 24 | 26 | 46 | |
| Controls | 10 | | | | 0/10 |
| 0.05 | 3 | 1 | 1 | 3 | 2/10 |
| 0.1 | | | | 1 | 9/10 |
| 0.25 | | | | | 10/10 |
| 0.5 | | | | | 10/10 |

D. In Vivo Activity With Escherichia Coli TO₂₆B₆

Groups of 10 male mice weighing about 22.5 g received intraperitoneally 0.5 ml of a 24 hour old culture in nutritive bouillon of Escherichia Coli TO$_{26}$B$_{6}$ diluted by 1/6 with distilled water and 1 hour, 5 hours and 24 hours later the mice received subcutaneously a determined amount of the product of Example 2. The number of dead mice during 8 days is reported in the following Table.

| Dose in mg | Dead after hours | | | | | Mice Alive on 8th day |
|---|---|---|---|---|---|---|
| | 21½ | 23 | 25 1/6 | 46 | 52 | |
| Controls | 10 | | | | | 0/10 |
| 0.5 | 1 | 1 | 1 | 1 | 1 | 5/10 |
| 1.0 | | | | | | 10/10 |
| 2.0 | | | | | | 10/10 |
| 3.0 | | | | | | 10/10 |

Various modifications of the products and processes of the invention may be made without departing from the spirit or scope thereof and it should be understood that the invention is intended to be limited only as defined in the appended claims.

We claim:

1. A compound of the formula

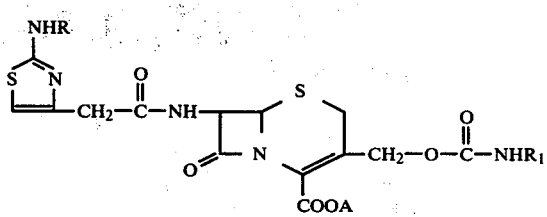

wherein R is selected from the group consisting of hydrogen and a group easily removable by acid hydrolysis or hydrogenolysis selected from the group consisting of tert.-butoxycarbonyl, trityl, benzyl, dibenzyl, trichloroethyl, carbobenzyloxy, formyl, trichloroethoxycarbonyl and 2-tetrahydropyranyl, R$_1$ is selected from the group consisting of hydrogen and alkyl of 1 to 4 carbon atoms and A is selected from the group consisting of hydrogen, alkali metal, an equivalent of alkaline earth metal and magnesium and a non-toxic, pharmaceutically acceptable organic amine base.

2. A compound of claim 1 wherein R is selected from the group consisting of tert.-butoxycarbonyl, trityl, dibenzyl, trichloroethyl and carbobenzyloxy.

3. A compound of claim 1 wherein R is selected from the group consisting of hydrogen and trityl, A is hydrogen and R$_1$ is selected from the group consisting of hydrogen and methyl.

4. A compound of claim 1 which is 3-carbamoyloxymethyl-7β-[2-(2-amino-4-thiazolyl)-acetamido]-ceph-3-eme-4-carboxylic acid.

5. A compound of claim 1 which is 3-methylcarbamoyloxymethyl-7β-[2-(2-amino-4-thiazolyl)-acetamido]-ceph-3-eme-4-carboxylic acid.

6. A compound of the formula

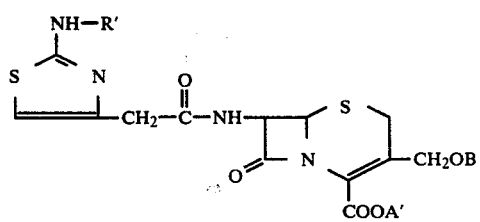

wherein R' is a group easily removable by acid hydrolysis or hydrogenolysis selected from the group consisting of tert.-butoxycarbonyl, trityl, benzyl, dibenzyl, trichloroethyl, carbobenzyloxy, formyl, trichloroethoxycarbonyl and 2-tetrahydropyranyl, A' is an alkali metal and B is selected from the group consisting of hydrogen and

and $R_2$ is a group easily removable by hyrolysis selected from the group consisting of trichloroacetyl, benzyl, p-methoxybenzyl and chlorosulfonyl.

7. An antibiotic composition comprising an antibiotically effective amount of at least one compound of claim 1 and an inert pharmaceutical carrier.

8. A composition of claim 7 wherein R is selected from the group consisting of hydrogen and trityl, A is hydrogen and $R_1$ is selected from the group consisting of hydrogen and methyl.

9. A composition of claim 7 wherein the compound is 3-carbamoyloxymethyl-7β-[2-(2-amino-4-thiazolyl)-acetamido]-ceph-3-eme-4-carboxylic acid.

10. A method of combatting bacterial infections in warm-blooded animals comprising administering to warm-blooed animals an antibacterially effective amount of at least one compound of claim 1.

11. The method of claim 10 wherein R is selected from the group consisting of hydrogen and trityl, A is hydrogen and $R_1$ is selected from the group consisting of hydrogen and methyl.

12. The method of claim 10 wherein the compound is 3-carbamoyloxymethyl-7β-[2-(2-amino-4-thiazolyl)-acetamido]-ceph-3-eme-4-carboxylic acid.

13. A compound of claim 1 wherein the organic amine base is selected from the group consisting of trimethylamine, triethylamine, methylamine, propylamine, N,N-dimethylethanolamine, tris-(hydroxymethyl)-methylamine, arginine and lysine.

* * * * *